Figure 1:
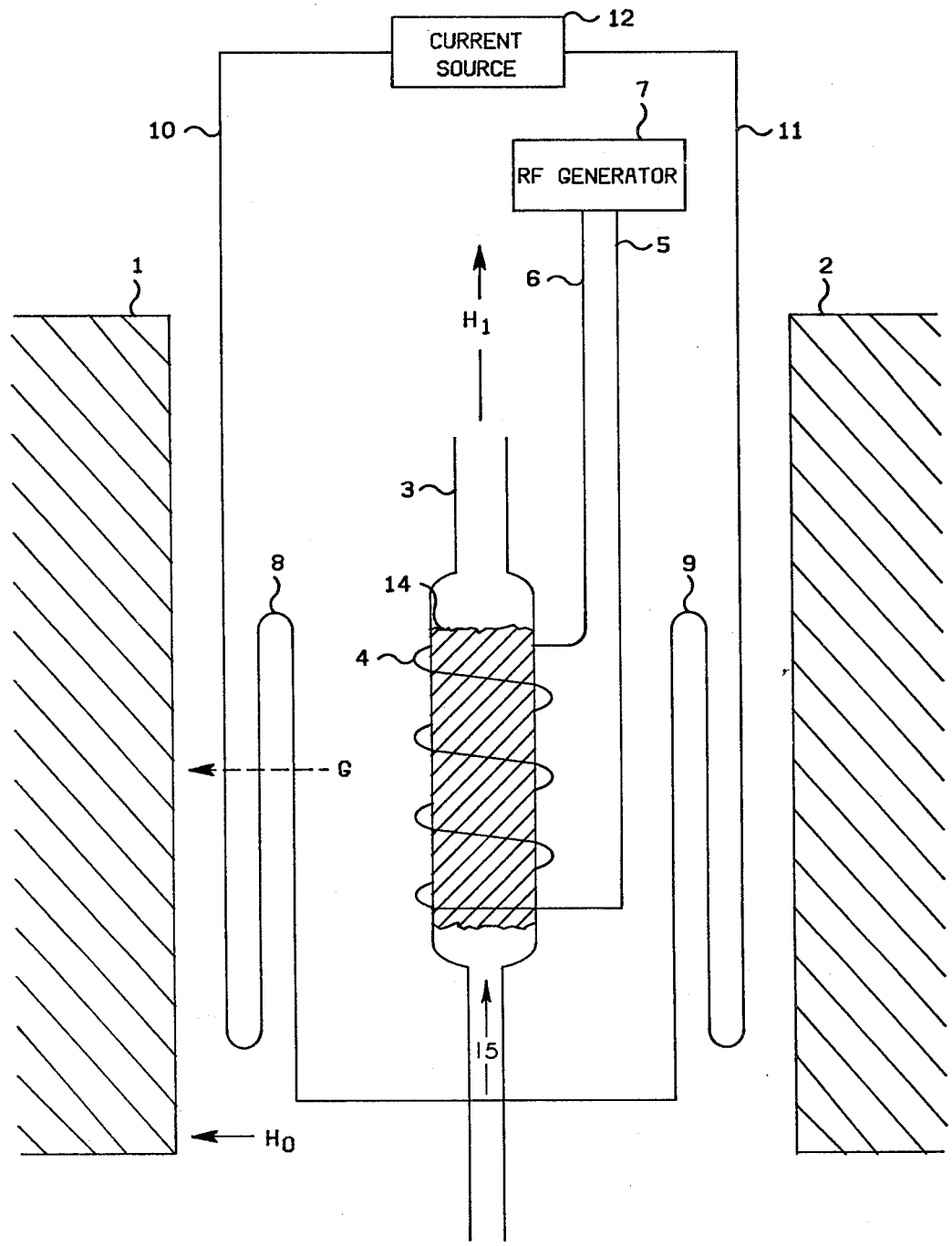

United States Patent [19]

Lauffer

[11] 4,424,487
[45] Jan. 3, 1984

[54] DISPERSION COEFFICIENT DETERMINATION

[75] Inventor: Donald E. Lauffer, Bartlesville, Okla.

[73] Assignee: Phillips Petroleum Company, Bartlesville, Okla.

[21] Appl. No.: 269,204

[22] Filed: Jun. 2, 1981

[51] Int. Cl.³ .................................................. G01R 33/08
[52] U.S. Cl. ....................................... 324/307; 324/300; 324/303
[58] Field of Search ................ 324/300, 303, 306, 307

[56] References Cited

U.S. PATENT DOCUMENTS

| | | | |
|---|---|---|---|
| 3,213,355 | 10/1965 | Woessner | 324/307 |
| 4,022,276 | 5/1977 | Dreher | 324/303 |
| 4,318,044 | 3/1982 | Mansfield | 324/300 |

FOREIGN PATENT DOCUMENTS 754280  8/1980  U.S.S.R. .............................. 324/300

Primary Examiner—Michael J. Tokar

[57] ABSTRACT

Dispersion coefficients of fluids in porous media are determined by NMR spin echo techniques while the fluid is flowing through the porous medium.

8 Claims, 7 Drawing Figures

DISPERSION COEFFICIENT DETERMINATION

This invention relates to the determination of the dispersion coefficient of fluids in porous formations. More specifically, this invention relates to the determination of flow characteristic properties of fluids in underground formations by utilizing NMR spectrometry.

BACKGROUND OF THE INVENTION

Post-primary oil recovery is of increasing importance for the energy demands in the world. Unfortunately, a large number of parameters, both chemical and physical in nature have influence on the efficiency and economy of a post-primary oil recovery process such as a surfactant flooding operation. Since large amounts of money have to be spent in the injection of fluids during such post-primary recovery a long time and sometimes years prior to any results which allow technical and economical calculations of the efficiency of the process, it is mandatory to obtain as many data and as detailed a set of information as possible from the underground reservoir.

One of the properties that is of critical importance is the dispersion coefficient of fluid in a given formation. If the quantity of a displacing fluid injected into the formation is too small the amount of oil recovered is dramatically reduced below the expected level. If the slug of displacing fluid on the other hand is too large, the process may become economically unfeasible. The dispersion coefficient is a significant property for the reservoir engineer to determine the quantity of displacement fluid needed for the specific reservoir. The dispersion coefficient of a fluid is influenced by the nature of the formation under a given flow condition. The transverse dispersion coefficient characterizes the spreading or mixing of a given volume of fluid transverse or perpendicular to the direction of flow. If the dispersion coefficient is large, this transverse spreading occurs fast and extensively. The longitudinal dispersion coefficient corrrespondingly characterizes the spreading or mixing of a given fluid volume in the direction of its flow. Again, a large longitudinal dispersion coefficient characterizes a fast and extensive spreading of a given fluid in its flow direction.

Generally, dispersion occurs during a dynamic (flowing) condition of the displacing fluid. There are a variety of mechanisms which lead to observable dispersion. These mechanisms can occur independent of each other or they can occur in a fashion which is dependent on the others. They include diffusion, hydrodynamic dispersion, eddies, mixing due to obstructions, dead-end pores, adsorption and recirculative flow. At low average fluid velocities, diffusion is the predominant dispersive mechanism. Hydrodynamic dispersion occurs during fluid flow by fluid particles and different positions moving relative to one another because of adhesion of the fluid to the container wall. If flow within the individual flow channels of the porous medium becomes turbulent, dispersion due to eddies results. Since flow channels in a porous medium are tortuous due to obstructions, dispersion occurs due to the changing distance between fluid particles even if the average velocity is constant. Dead-end pores function as storage volumes for fluid elements and thus result in dispersion during fluid flow. Adsorption and desorption of fluid molecules on the pore walls result in dispersion. Channels which connect regions of high and low velocities can also produce dispersion by a Venturi effect. Thus, it will be seen that in the limit as fluid velocity approaches zero, dispersion becomes diffusion.

The techniques known in the prior art for the determination of dispersion coefficients generally contain inherent inaccuracies due to boundary effects due to the laboratory sample size. A method is therefore needed which is capable of determining dispersion coefficients which are independent of sample boundaries in order to provide more realistic information on the dispersion processes which actually occur in a reservoir formation.

By use of a pulsed nuclear magnetic resonance (NMR) technique, this invention provides a means of determining transverse and longitudinal dispersion coefficients which are independent of sample boundaries since the period of time during which the measurements are made is selected so that the number of molecules interacting with the sample boundary is small. Pulsed NMR techniques for determining diffusion coefficients are well known in the art; however, this invention provides a means of determining dispersion coefficients because the measurements are conducted during a dynamic (flowing) condition of the displacing fluid. A knowledge of the transverse and longitudinal dispersion coefficients is of particular importance in tertiary oil recovery by assisting reservoir engineers in designing the nature and size of slugs of displacing fluid which will most efficiently displace the residual crude oil.

The NMR technique which is employed to study the displacing fluids during the flow through a porous rock formation according to this invention employs the well known "spin echo" technique disclosed in U.S. Pat. Nos. 2,705,790 and 3,109,986.

STATEMENT OF THE INVENTION

It is thus one object of this invention to provide a methód for determining the dispersion coefficient of fluids in porous materials.

Another object of this invention is to provide an accurate method for determining both the transverse and the longitudinal dispersion coefficient of fluids in porous materials.

Figure 2:
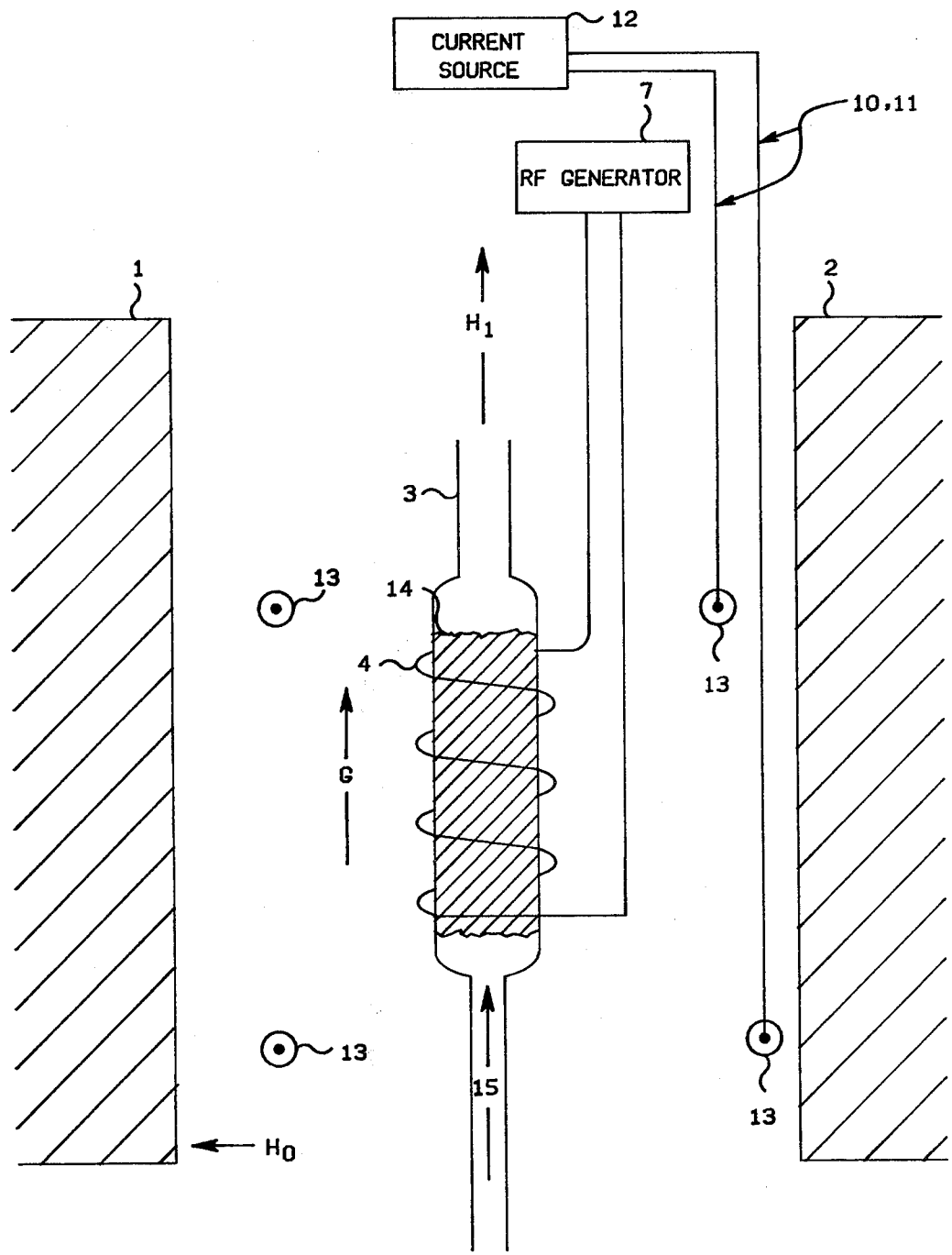
Figure 3:
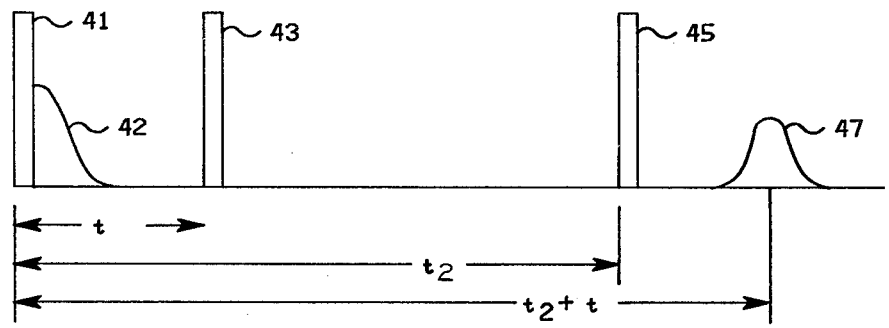

These and other objects, advantages, details, features and embodiments of this invention will become apparent to those skilled in the art from the following detailed description thereof, the appended claims as well as the drawings in which;

FIG. 1 is a schematic representation of an NMR spectrometer apparatus for determining the transverse dispersion coefficient of a sample, FIG. 2 is a representation similar to that of FIG. 1, however, for the determining of the longitudinal dispersion coefficient of a sample, FIG. 3 illustrates the time relationship between the various pulses of a three pulse NMR spin echo measurement, FIGS. 4–7 represent schematic representations of the orientation of the magnetic vector in a rotating coordinate system at the various stages of a three pulse NMR spin echo measurement.

In accordance with this invention it has now been found that it is possible to determine the dispersion coefficient of a fluid in a sample of porous material by subjecting the sample to an NMR spin echo measurement while the fluid on which the NMR spin echo measurement is carried out is flowing through the sample. It has been found that above a certain flow velocity of this fluid the dispersion coefficient changes substantially with the flow velocity.

Referring now to FIG. 1, a static magnetic field of magnitude $H_o$ is produced by an electromagnet with opposing poles 1 and 2. A sample holder 3 containing the desired porous rock 14 and displacing fluid 15 flowing therethrough is positioned in the air gap between the opposing poles of the electromagnet. A wire coil 4 encompasses sample holder 3 and the contained sample. Leads 5 and 6 connect coil 4 to a source 7 of alternating current of frequency which can be varied but is normally set at a particular value. Alternating current flowing in coil 4 produced alternating magnetic field pulses $H_1$ which are perpendicular to static magnetic field $H_o$. Secondary field coils 8 and 9 (opposing Helmholtz coils) attached through leads 10 and 11 to current source 12 produce a constant magnetic field gradient G superpositioned on $H_o$.

Referring now to FIG. 2, a simplified representation of the device employed to measure longitudinal dispersion coefficients, electromagnetic poles 1 and 2, alternating current source 7 and corresponding coil 4, and sample holder 3 and contained sample are the same as above described for FIG. 1. This embodiment of the invention employs current elements 13 which are positioned as in FIG. 2 so as to be perpendicular to the plane of the diagram. Current elements are connected through leads 10 and 11 to current source 12 which produces a constant magnetic field gradient G.

If a spinning nuclear magnet is placed in a static magnetic field the axis of the nuclear magnet will tend to orient with the applied magnetic field gradient, but since the nucleus has angular momentum, the net effect is that the rotational axis precesses around the applied magnetic field. The frequency of precessing which is characteristic of a particular type of nucleus is called the Larmor frequency and is equal to the product of the gyromagnetic ratio, $\gamma$, and the magnetic field strength, $H_o$. If a sinusoidal radio frequency magnetic field $H_1$ is applied normal (at right angle) to the static field and is equal to the Larmor frequency of the nucleus, the well-known condition called "resonance" results and a net absorption of magnetic energy is observed on the detector.

Figures 4, 5:
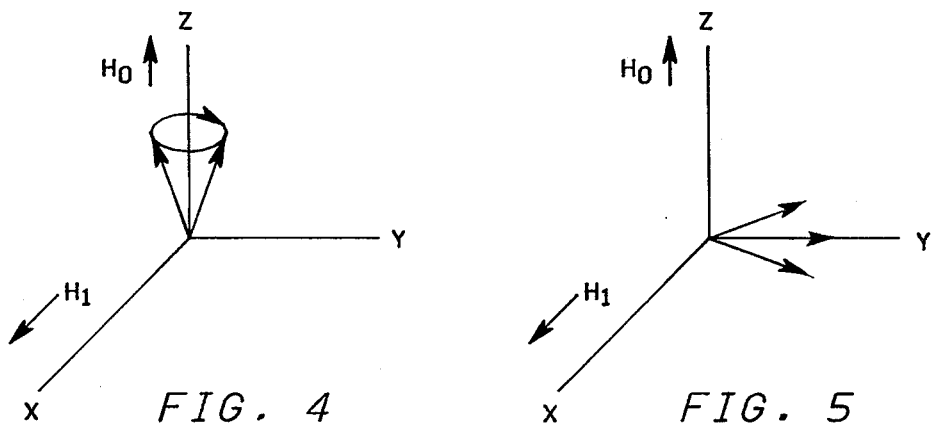
Figures 6, 7:
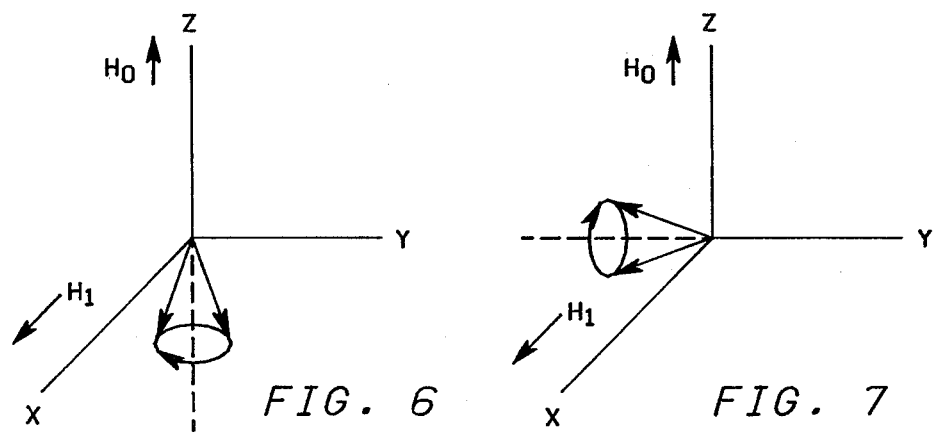

The spin echo technique employed in this invention is most easily described by use of a reference frame which rotates about the direction of $H_o$ at a frequency equal to the Larmor frequency. By convention, the z-axis and the x-axis of the rotating reference frame are defined to coincide with $H_o$ and $H_1$ respectively. FIGS. 4-7 are highly simplified diagrams representing the behavior of the precessing axis of the nuclear magnet relative to the rotating reference frame during the experiment. FIG. 4 represents the macroscopic moment of the precessing nuclear magnet in the static magnetic field $H_o$. Any relaxation of the NMR signal is due to spin-spin and spin-lattice interactions, as well as, dispersion. An initial radio frequency pulse is introduced through coil 4 (FIGS. 1 and 2) at an amplitude and for a duration sufficient to rotate the precessing nuclear magnet by 90° to the y-axis (FIG. 5). Relaxation which occurs after the 90° pulse is dominated by spin-spin interactions which predominate for porous rock samples when magnetization is perpendicular to magnetic field $H_o$. Dephasing or fanning out of the magnetization vector as a result of interactions with gradient G is represented in FIG. 5 by the three components. A second radio frequency pulse is applied through coil 4 at an amplitude and for a duration sufficient to rotate the precessing nuclear magnet by 180° around the x-axis (FIG. 7). If time t represents the time elapsed between the 90 degree pulse and the 180 degree pulse, then after an additional time t after the 180 degree pulse the magnetization is refocused on the negative y-axis, thus producing the observed spin echo. The amplitude of the measured spin echo will be the same as the original NMR signal decreased by the effects of relaxation, including the dispersive effects.

Thus, it will be readily apparent that if no dispersion occurred during the pulsed experiment, the amplitude of the spin echo after a time 2t is given by the equation $$M = M_o \exp(-2t/T_2)$$

where M is the initial magnetization at time 0 and $T_2$ is the spin-spin relaxation time. Therefore, the amplitude of the spin echo when dispersion has occurred is given by the equation $$M = M_o \exp[-2t/T_2 - \gamma^2 G^2 D(2t)^3/12]$$

where G is a constant magnetic field gradient applied during the time interval 2t. $\gamma$ is the gyromagnetic ratio of the nucleus, and D is the transverse dispersion coefficient.

For the determination of the longitudinal dispersion coefficient, the equation differs slightly from the transverse dispersion because both the fluid flow and longitudinal dispersion occur along the x-axis, therefore, the gradient of the z-component of the magnetic field must be a constant in the x-direction. The expression for the magnetization is then given by the equation $$M = M_o \exp[-2t/T_2 - \gamma^2 G^2 D_1(2t)^3/12 + i3\gamma GVt^2]$$

where $D_1$ is the longitudinal dispersion coefficient and V is the fluid velocity.

Both D and $D_1$ are functions of the fluid velocity.

It is within the scope of the invention to employ a sequence of three 90° pulses (see FIG. 3) rather than the 90°–180° pulse sequence described previously. Often it is the case in reservoir cores that the spin-spin relaxation time ($T_2$) is small (10 to 25 milliseconds). This condition makes it difficult to acquire data for dispersion times of 50-100 milliseconds. Such times are frequently required, however, since the molecules must have sufficient time to travel through tortuous paths for the effect of dispersion to be measured. The advantage of the three-90° pulse experiment is that the signal relaxes by $T_1$ processes (spin-lattice relaxation) rather than by $T_2$ processes (spin-spin relaxation) during the interval between the second and third 90° pulses. Since $T_1$ is normally greater than $T_2$ in reservoir rocks, sufficiently long dispersion times can usually be obtained by adjusting the interval between the 2nd and 3rd 90° pulses.

The technique for implementing the three-90° pulse experiment is similar to the 90°–180° pulse experiment. The first 90° pulse is applied at time 0. Instead of applying a 180° pulse at time t, a second 90° pulse is applied to rotate the nuclear magnetization to the negative z-direction (FIG. 6). To complete the experiment a third 90° pulse is applied at time $t_2$. This pulse restores the magnetization to the x,y plane (FIG. 7) from which refocusing of the magnetization produces a "stimulated" spin echo.

If no dispersion occurred during the pulsed experiment, the amplitude of the "stimulated" spin echo after a time $t+t_2$ is given by the equation [D. E. Woessner, J. Chem. Phys. 34, 2057 (1961)]

$$M = M_o \exp[-2t/T_2 - (t_2-t)/T_1]$$

where $M_o$ is the initial magnetization and $T_1$ and $T_2$ are the spin-lattice and spin-spin relaxation times, respectively. The amplitude of the "stimulated" spin echo when transverse dispersion occurred is given by the equation $$M = M_o \exp[-2t/T_2 - (t_2-t)/T_1 - \gamma^2 G^2 D t^2(t_2-t/3)]$$

where G is the constant gradient, $\gamma$ is the gyromagnetic ratio of the nucleus, and D is the transverse dispersion coefficient.

For the determination of the longitudinal dispersion, the amplitude of the stimulated spin echo is given by the equation $$M = M_o \exp[-2t/T_2 - (t_2-t)/T_1 - \gamma^2 G^2 D_1 t^2(t_2-t/3) - i\gamma GVtt_2]$$

where $D_1$ is the longitudinal dispersion coefficient, and V is the fluid velocity in x-direction.

The instruments which are useful in determining dispersion coefficients according to this invention are selected from well known broad band NMR spectrometers, a number of which are commercially available. The spectrometer is coupled to a high speed digitizer (e.g., 10 bits, 500 kHz). The magnet of the spectrometer is of reasonably high resolution; the gradient of the magnet is at least 1 order of magnitude less than the imposed gradient G. The gap in the magnet is large, e.g., greater than 4 centimeters, in order for the sample, rf coils and secondary field coils, to be inserted therein.

In order to determine dispersion coefficients according to this invention, it is necessary that the drive fluid flowing through the sample is of such a composition that NMR signal is obtained. Since aqueous solutions or organic solutions are normally employed as drive fluids, proton resonance is observed.

The porous rock sample to be studied by means of this invention is generally cylindrical in shape with a length of about 2-5 centimeters and the diameter of about 1-2 centimeters. The size of the porous rock sample is not critical to this invention. The size is important only in that it should be sufficiently small to fit conveniently into the cavity of the instrument and large enough to give a representative sample and to be easily prepared with sufficient structural strength to be handled.

It is necessary to encase the porous rock sample in a tightly fitting film in order to prevent the drive fluid passing therethrough from draining from the sample and from exiting the sample from the pores along the edges thereof. The encasing material for the porous rock samples is selected from film-forming polymeric materials which are impervious to the fluids in the porous rock sample. Such encasing materials can be applied to the porous rock samples as tightly fitting sleeves or as curable polymer formulations.

Examples of such materials include preformed tubes (sleeves) of polyethylene, poly(vinyl chloride), poly(tetrafluoroethylene), butadiene-styrene copolymers, as well as, curable materials, such as epoxy resin, which can be applied as a semisolid thin film and subsequently cured to a tough impervious coating. It is not necessary that these encasing materials be proton-free, since the useful materials are solid in nature and do not produce spin echoes even though they do have protons. It is necessary that these films fit very tightly on the rock samples; films of liquid between the encasing material and the porous rock sample interfere with the determination. It is desirable, therefore, to use semisolid curing materials, such as epoxy resin, which penetrate the porous rock sample to a slight extent prior to curing and thus avoid the problem of liquid film between the rock surface and the encasing film. An alternative method of encasing the rock sample employs a tube of suitable polymeric material which shrinks on contact with heat. The sample of rock is placed in the tube which is then exposed to heat which shrinks the polymeric material to form a tightly fitting sleeve around the rock sample.

This invention is generally useful with a wide variety of non-magnetic porous rocks which are normally associated with natural formations which could be reservoirs for organic fluids, such as crude oil. Since ferromagnetic materials are known to interfere with NMR measurements, porous rocks useful in this invention will contain a maximum of about 3 percent by weight based on total porous rock, and preferably will contain less than 1 percent, ferromagnetic material, such as iron.

This invention is preferably carried out at a flow rate of the fluid of from about $0.01 \times 10^{-3}$ to about $1.0 \times 10^{-2}$ cm$^3$/sec through the generally cylindrical sample described above. It is recognized that the optimum flow rate through the sample will be dependent, in part, on the cross-sectional area of the sample. With a cylindrical sample of 1.25 cm diameter, a fluid flow rate of $4 \times 10^{-3}$ cm$^3$/sec roughly corresponds to frontal velocity (velocity at the interface between the drive fluid and the displaced fluid) of about 10 ft/day, which value is a commonly used value for actual reservoir application in which drive fluid is pumped down an injection well at a rate so as to provide approximately 10 ft/day frontal velocity and the displaced fluid and, eventually, drive fluid are recovered from a remotely located producing well.

Though the present invention can be employed over the above-identified wide range of flow rates through the sample, it is recognized that, at the lower flow rates, dispersion coefficients do not differ greatly from diffusion coefficients. It is at higher flow rates, e.g., above about $4 \times 10^{-3}$ cm$^3$/sec for a 1.25 cm diameter sample, that dispersion coefficients are significantly different from diffusion coefficients and, hence, this invention is particularly valuable. Thus, the reservoir engineer having in hand the dispersion coefficients characteristic of his particular drive fluid and reservoir rock determined by means of this invention can economically design conditions of flow rate and volume of drive fluid for his application. Such a determination may involve a variety of computations such as production modelling. In these computations diffusion coefficients appear, such as in simple diffusion equations. Since the flow rate of fluids introduced into the formation can be manipulated within limits, better predictions concerning e.g. the effectiveness of the front of the introduced material can be made. The dispersion coefficient is used in the modelling instead of the diffusion coefficient (at a given flow rate).

EXAMPLE

The following example demonstrates the use of this invention in determining the transverse dispersion coefficient of brine in Berea sandstone.

The instrument employed in the measurement of dispersion coefficient was a custom-built, pulsed, single coil nuclear magnetic resonance spectrometer of conventional design capable of producing a 90° pulse in 5-6 microseconds and employing a 12 inch (30.5 cm) magnet (from Varian Associates, Palo Alto, Calif.) with a 1.75 inch (4.4 cm) gap. The rf coil consisted of 6 to 7 turns of #14 enameled copper wire wound snugly around the sample container; the coil was tuned in a parallel circuit. The power supply connected to the gradient coils (Bruker Scientific, Inc., Palo Alto, Calif.) was a current-regulated, D.C. power supply (Lambda Electronics Corp., Melville, Long Island, N.Y., Model LP-410A-FM). The current from the power supply was determined accurately by measuring the potential difference across a one ohm resistor.

The measurements were conducted at 30 mHz (7,000 Gauss). A gradient range of 0.5 Gauss/cm to 6 Gauss/cm was employed in the measurement. The gradient was calibrated according to the procedure of Carr and Purcell, Phys. Rev. 94, 630 (1954).

A programmable, pulse delay unit was used to trigger the NMR transmitter and the data acquisition system.

The signal from the rf coil was amplified using a high impedance preamplifier of conventional design and a postamplifier (Model ITA-34-30-08-50 from Varian Associates, Palo Alto, Calif.) and was amplitude detected using temperature-compensated diodes and digitized by an analog-to-digital converter at a rate of 500 kHz. The digitized data were accumulated in a computer (Model 2100 from Hewlett-Packard) over approximately 50 acquisitions to enhance the signal-to-noise ratio. The base line of the accumulated signal was subtracted from the total signal to give the spin echo amplitude the maximum value of which was determined by at least squares parabolic fit.

A sample of Berea sandstone (19 percent porosity and 298 millidarcy permeability) was prepared as a cylinder 1.25 cm diameter and 2.75 cm length. The outer curved surface of the cylinder was sealed by applying a sleeve of surface-irradiated heat-shrinkable polyolefin tubing (Alpha Tubing Co.) and heating with a 1000 Watt heat gun for about one minute. The heat-shrinkable tubing sealed glass tubing connections to the open ends of the enclosed cylinder. The sample was filled with sodium chloride brine (1200 ppm NaCl in water) by pressurizing at 13,500 kPa.

Brine (1200 ppm NaCl in water) was pumped through the porous rock sample at constant flow rates and the amplitude of the spin echo was measured during flow. Transverse dispersion coefficients (calculated from spin echo amplitude) determined for various rates of flow are recorded in the following table.

TABLE

| Flow Rate, $\times 10^3$, cm$^3$/sec$^{(A)}$ | Tr. Desp. Coeff., $\times 10^5$, cm$^2$/sec |
|---|---|
| 0.011 | 0.94–1.06 |
| 0.125 | 1.0–1.1 |
| 0.23 | 1.0–1.08 |
| 0.40 | 0.96–1.12 |
| 0.80 | 1.07–1.13 |
| 1.2 | 1.1–1.21 |
| 2.6 | 1.05–1.18 |
| 4.0 | 1.04–1.2 |
| 7.0 | 1.19–1.29 |
| 8.0 | 1.2–1.36 |
| 9.4 | 1.28–1.4 |

$^{(A)}$Based on cross sectional area of 1.25 cm sample.

The above data demonstrate that transverse dispersion coefficient increases as flow rate increases, slowly at first, then more rapidly. Up to about $4\times 10^{-3}$ cm$^3$/sec little difference exists between transverse dispersion coefficient and restricted diffusion coefficient ($1.0\times 10^{-5}$ cm$^2$/sec). Above about $4\times 10^{-3}$ cm$^3$/sec significant differences between dispersion and diffusion coefficients appear. Thus, at brine flow rates up to those "normally" employed in crude oil recovery ($4\times 10^{-3}$ cm$^3$/sec or about 10 ft/day based on frontal movement in actual reservoir conditions based on sample cross section in this experiment) transverse dispersion coefficients are only slightly higher than diffusion coefficients, but as flow rates increase dispersive forces other than diffusion become more and more significant.

Reasonable variations and modifications which will become apparent to one skilled in the art can be made in this invention without departing from the spirit and scope thereof.

I claim:

1. A method for determining the dispersion coefficient of fluid in porous media comprising
   (a) positioning a sample representative of said porous media in an NMR spectrometer,
   (b) causing said fluid to flow through said so positioned sample, said fluid being capable of exhibiting a detectable response in an NMR spectrometer measurement,
   (c) carrying out an NMR spin echo measurement while said fluid is glowing and while said flowing fluid is subjected to a magnetic field gradient and obtaining a spin echo signal,
   (d) determining the dispersion coefficient from the spin echo signal obtained.

2. A method in accordance with claim 1 wherein said fluid is flowing through said sample in a main direction which is essentially 90° to the main constant magnetic field of the NMR spectrometer and wherein said sample during said spin echo measurement is subjected to a radio frequency electromagnetic pulse generated in a coil surrounding said sample and having a coil axis essentially parallel to said main direction.

3. A method in accordance with claim 2 wherein during said spin echo measurement said sample is subjected to a further magnetic field generating a gradient in magnetic field strength having a direction essentially parallel to the main magnetic field and wherein the transverse dispersion coefficient of the sample is determined.

4. A method in accordance with claim 2 wherein during said spin echo measurement said sample is subjected to a further magnetic field generating a gradient in the magnetic field strength having a direction essentially orthogonal to the main magnetic field and parallel to the coil axis and wherein the longitudinal dispersion coefficient of the sample is determined.

5. A method in accordance with claim 3 wherein a plurality of three 90° pulse spin echo measurements is carried out, wherein the spin echo signal is obtained as a function of the magnetic field gradient and wherein said transverse dispersion coefficient is determined from said function.

6. A method in accordance with claim 4 wherein a plurality of three 90° pulse spin echo measurements is carried out, wherein the spin echo signal is obtained as a function of said magnetic field gradient and wherein said longitudinal dispersion coefficient is determined from said function.

7. A method for determining the dispersion coefficient of fluid in porous media comprising
    (a) positioning a sample representative of said porous media in an NMR spectrometer,
    (b) causing said fluid to flow through said so positioned sample, said fluid being capable of exhibiting a detectable response in an NMR spectrometer measurement,
    (c) carrying out an NMR spin echo measurement while said fluid is flowing and while said flowing fluid is subjected to a magnetic field gradient and obtaining a spin echo signal,
    (d) obtaining the spin echo signal as a function of said magnetic field gradient, and
    (e) determining the dispersion coefficient from said function.

8. A method for determining the dispersion coefficient of fluid in porous media comprising
    (a) positioning a sample representative of said porous media in an NMR spectrometer,
    (b) causing said fluid to flow through said so positioned sample, said fluid being capable of exhibiting a detectable response in an NMR spectrometer measurement,
    (c) carrying out an NMR spin echo measurement while said fluid is flowing and while said flowing fluid is subjected to a magnetic field having a constant magnetic field gradient applied and obtaining a spin echo signal,
    (d) obtaining the spin echo signal as a function of said magnetic field gradient, and
    (e) determining the dispersion coefficient from said function.

* * * * *

UNITED STATES PATENT AND TRADEMARK OFFICE
CERTIFICATE OF CORRECTION

PATENT NO. : 4,424,487
DATED : January 3, 1984
INVENTOR(S) : Donald E. Lauffer

It is certified that error appears in the above—identified patent and that said Letters Patent is hereby corrected as shown below:

Column 8, Claim 1, line 38, "glowing" should be --- flowing ---.

Signed and Sealed this

Eighth Day of May 1984

[SEAL]

Attest:

GERALD J. MOSSINGHOFF

*Attesting Officer*     *Commissioner of Patents and Trademarks*